United States Patent [19]
Skakkebæk et al.

[11] Patent Number: 5,492,891
[45] Date of Patent: Feb. 20, 1996

[54] METHOD FOR TREATMENT OF PATIENTS WITH CHRONIC LIVER DISEASE

[75] Inventors: Niels E. Skakkebæk, Farum; Søren Moeller, Frederiksberg C., both of Denmark

[73] Assignee: Novo Nordisk A/S, Bagsvaerd, Denmark

[21] Appl. No.: 199,319

[22] PCT Filed: Aug. 18, 1991

[86] PCT No.: PCT/DK92/00245

§ 371 Date: Mar. 2, 1994

§ 102(e) Date: Mar. 2, 1994

[87] PCT Pub. No.: WO93/04694

PCT Pub. Date: Mar. 18, 1993

[30] Foreign Application Priority Data

Sep. 5, 1991 [DK] Denmark .................. 1554/91

[51] Int. Cl.⁶ ............ A61K 38/27; C07K 14/61
[52] U.S. Cl. ............. 514/12; 514/21; 514/838; 530/399
[58] Field of Search .............. 514/12, 21, 838, 514/893, 894; 530/399, 839

[56] References Cited

U.S. PATENT DOCUMENTS 4,898,857  2/1990  Aroonsakul .................. 514/171

FOREIGN PATENT DOCUMENTS

WO89/09614  10/1989  WIPO.
WO91/11195   8/1991  WIPO.

OTHER PUBLICATIONS

Giordano et al. "Somatomedin (Sm) Behavior In Patients With Chronic Liver Diseases" Acta Endocrin. Suppl. 199 262 1975.

Moller et al. "Effect of Recombinant Human Growth Hormone (rHGH) on Insulin-Like Growth Factor (IGF-1) In Patients w/Cirrhosis of The Liver" J. Hepatol 13(Suppl 2) S146 1991.

Schimpff et al. "Serum Somatomedin Activity Measured As Sulphation Factor In Peripheral, Hepatic & Renal Veins of Patients with Alcoholic Cirrhosis" Acta Endocrin. 88(4) 729–736 1978.

Schimpff et al. "Somatomedin Production In Normal Adults & Cirrhotic Patients" Acta Endocrin 86(2) 355–362 1977.

Eversmann et al. "Somatomedin-B In Acromepoly, Liver Cirrhosis, & Renal Failure" Acta Endocrin Suppl. 212 p. 186 Abstract #320 1977.

*Primary Examiner*—Michael G. Wityshyn
*Assistant Examiner*—Nancy J. Degen
*Attorney, Agent, or Firm*—Steve T. Zelson; Cheryl H. Agris

[57] ABSTRACT

Patients with chronic liver disease and consequently very low concentrations of IGF-1 in the blood, in spite of increased GH concentrations, are treated with periodically injections of hGH for a period both parameters being individually adjusted for the patients.

3 Claims, 1 Drawing Sheet

METHOD FOR TREATMENT OF PATIENTS WITH CHRONIC LIVER DISEASE

The present invention concerns a method for treatment of patients with chronic liver disease and an agent for use in the method.

The frequency of patients with chronic liver diseases is unknown, but in Europe the number of patients with newly recognized liver diseases seems to be increasing concurrently with the increasing consumption of alcohol.

The chronic liver diseases includes the alcoholic liver cirrhosis, which is dominating in number, liver cirrhosis caused by chronic infection after acute inflammation of the liver and last and more seldom occurring immunological liver diseases characterized by chronic inflammation without known reason.

Especially the alcoholic liver cirrhosis constitutes today a still increasing problem in national health care. The primary treatment available is of preventing character such as abstinence from alcohol in order to prevent aggravation of the disease. Once the alcoholic liver cirrhosis has taken place the present possibilities of therapeutic treatments are very limited.

Normally the alcoholic liver cirrhosis develops gradually and is often preceded by several years of alcoholic abuse. The development of cirrhosis hepatis is preceded by a state of increasing accumulation of fat in the liver (steatosis hepatis). This state is reversible and the liver can be normalised if consumption of alcohol is terminated. However, if the abuse goes on then the liver tissue will gradually be transformed to connective tissue which leads to badly working liver tissue and consequently reduced function of the liver.

Under normal conditions the liver plays an important role in metabolism including accumulation of nutrients, transformation and excretion of waste products, production of proteins which are important for the composition and coagulation of the blood. Furthermore, the liver functions as a gland by producing and secreting gall as well as various hormones comprising IGF-1. In case of reduced function of the liver all this above mentioned functions are influenced in various degrees and the patient with chronic liver disease is especially characterized by having in the blood very low concentrations of the proteins and hormones which are produced in the liver. A reduced concentration of the protein albumin in the blood is of importance for the development of edema in the abdominal cavity such as ascites and in the legs, which problems are often connected with patients having a chronic liver disease. A reduced capability of production of coagulation factors, which are important for the normal coagulation of blood, leads to an increased tendency of bleeding in these patients and this tendency is used to express the degree of failure of the liver.

Patients having a chronic liver disease are furthermore characterized by having a distorted regulation of a number of endocrine systems. As one result among others, is the ascertainment of greatly reduced concentrations of the growth factor IGF-1 (Insulin-like Growth Factor-1) in the blood. IGF-1 is a hormone which is mainly produced in the liver upon stimulation by GH (Growth Hormone) from the pituitary gland. IGF-1 plays an important role for the growth and development of children. Further IGF-1 is important for metabolism by stimulation of protein synthesis in the liver and other organs, besides it is important for regulation of the carbohydrate metabolism. IGF-1 is synthesized and released from the liver caused by GH stimulation, and children with GH-deficiency are characterized by having very low concentrations of IGF-1 in the blood.

When a chronic liver disease has reached the state of incipient failure of the liver then the capability of the liver to produce IGF-1 is reduced and therefore very low concentrations of IGF-1 is found in the blood. It appears that there is a positive correlation between the reduction in IGF-1, the degree of the liver disease and the prognosis of the patients. As a physiological reaction to the above mentioned conditions increased basic GH concentrations are found in the blood of these patients. However, these concentrations are not capable of normalizing the very low IGF-1 concentrations.

Cirrhosis of the liver is associated with a very serious prognosis. About one third of the patients will die within 2 years after a diagnosis has been made. Average expectation of life for these patients is under 4 years and adjusted for age the average death rate for this patients is 10 times higher than normal. The factors of particular importance for this prognosis seem to be reduced serum albumin, IGF-1 and prothrombin which last factor leads to reduced coagulation.

Today the medical treatment of advanced cirrhosis of the liver is only symptomatic and directed against complications such as ascites, varices connected to the gullet and hepatic coma. Apart from total abstinence from alcohol all other attempts to stop or change the course of the cirrhotic process have only given poor results. Also numerous cures using particular dietetic treatments, multivitamin preparations, fructose etc. which cures were supposed to have an influence on the liver function, have shown to be without result.

As mentioned above, in patients with liver cirrhosis the concentration of IGF-1 in the blood is very low, while GH, which stimulates the synthesis and release of IGF-1 from the liver, is present in a very high concentration. Therefore it seems that GH is present in relative excess, however an excess that cannot be used and which consequently is excreted in the urine.

In the light of the poor possibilities given by the various treatments known up till now, we have performed clinically controlled trials on the subject. Surprisingly, during this trials, we have found that in spite of the above mentioned increased concentrations of GH in the blood of the patients leading to increased excretion of GH, then it is possible by administration of GH to the already existing surplus to increase the also above mentioned very low IGF-1 concentration considerably.

The invention is further explained but not limited by the following example.

EXAMPLE 1

Figure 1:
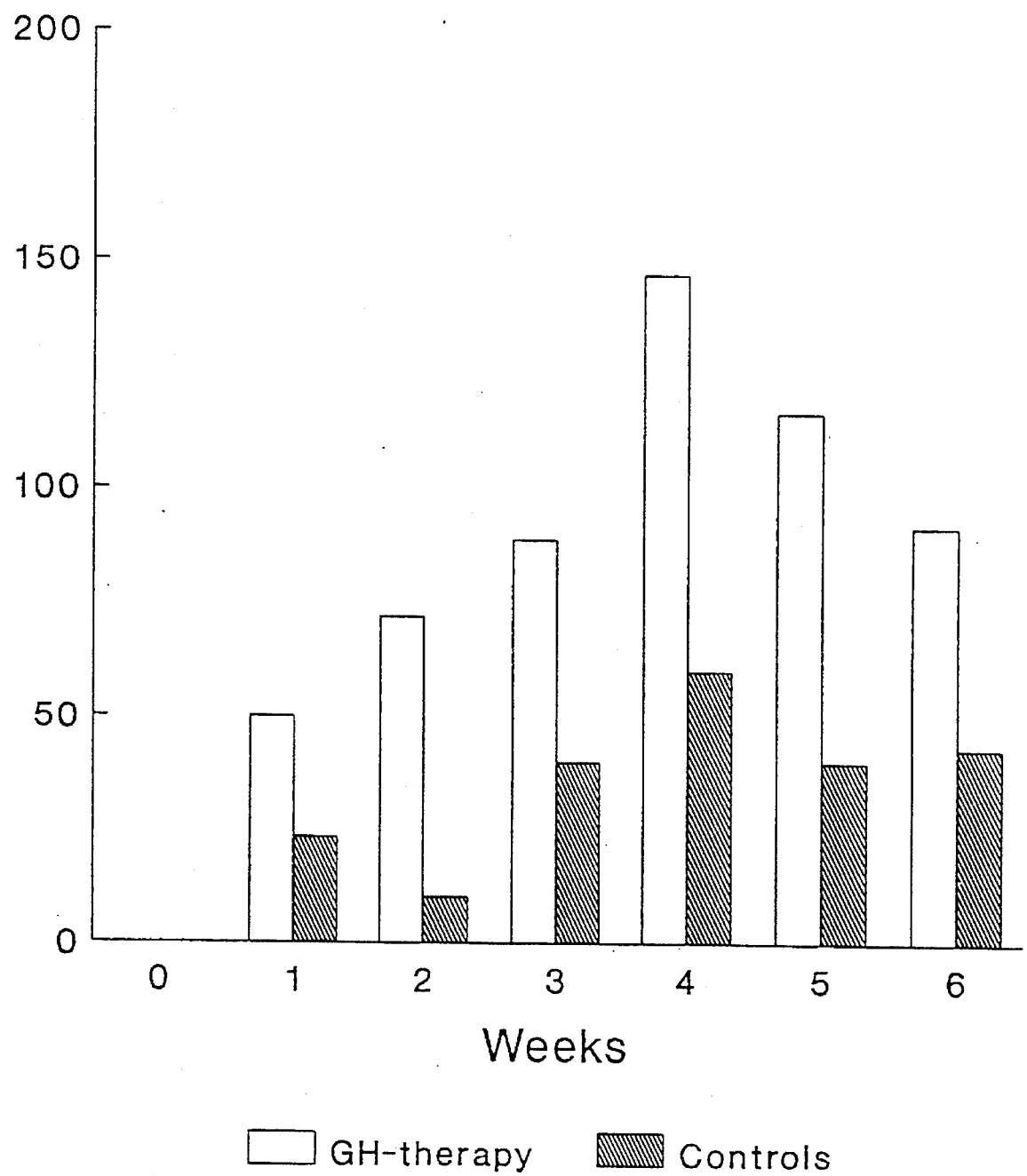
FIGURE 1 shows a comparison of the percental rise in IGF-1 between patients who did and did not receive GH therapy.

20 consecutive male patients with alcoholic cirrhosis were evenly randomized to either conventional medical treatment supplemented with injections of recombinant human growth hormone (rhGH) or conventional medical treatment alone. The treatment period lasted for 6 weeks in which measurements of the effect parameters were performed twice weekly. In order to achieve optimal compliance all patients, both the GH-group and the control group, were hospitalized during the trial. The injections of rhGH were administered by the nursing staff.

The patients in the control group had a conventional medical treatment comprising vitamin B and thiamine in all 6 weeks. The patients in the GH-group had the same treatment but as a decisive factor supplemented with injections of rhGH (Norditropin®), administered subcutaneously in a dose of 4 IU twice daily for all 6 weeks.

After the end of the trial period the following results for the main parameter IGF-1 were found:

TABLE 1

| WEEKS | IGF-1 (nmol/l) Mean | |
| --- | --- | --- |
| | GH-GROUP | CONTROL GROUP |
| Baseline | 3.6 | 3.0 |
| 1 | 5.4 | 3.7 |
| 2 | 6.2 | 3.3 |
| 3 | 6.8 | 4.2 |
| 4 | 8.9 | 4.8 |
| 5 | 7.8 | 4.2 |
| 6 | 6.9 | 4.3 |

From the above results it can be seen that even if the patients had an increased concentration of GH in the blood it was possible to increase the IGF-1 concentration in the patients belonging to the GH-group compared to the patients belonging to the control group (FIGURE 1). It is very likely that this increased IGF-1 concentration has a beneficial influence on the course of the liver disease and on the clinical state and prognosis of the patients. It is believed that the present invention creates an important contribution to the conventional treatment of patients with chronic liver disease, which treatment as it is known to day has very little possibilities and a very poor prognosis.

When using this method it is to be understood that the parameters e.g. period of treatment and daily doses should be individually adjusted to the patients, based on a medical examination and judgement.

We claim:

1. A method for treating a patient with alcoholic cirrhosis of the liver and consequently low concentrations of IGF-1 in the patient's blood comprising treating the patient with an amount of human growth hormone effective to increase the level of IGF-1 in the blood of said patient.

2. The method according to claim 1 in which the human growth hormone is injected.

3. A method for increasing the concentration of IGF-1 in a patient with low concentrations of IGF-1 in the patient's blood comprising treating the patient with an amount of human growth hormone effective to increase the level of IGF-1 in the blood of said patient.

* * * * *